United States Patent
Walter

(10) Patent No.: US 8,702,723 B2
(45) Date of Patent: Apr. 22, 2014

(54) DEVICE FOR PERFORMING EXAMINATIONS AND SURGICAL INTERVENTIONS ON THE UTERUS

(75) Inventor: Christian Walter, Emmingen-Liptingen (DE)

(73) Assignee: Karl Storz GmbH & Co. KG (DE)

( * ) Notice: Subject to any disclaimer, the term of this patent is extended or adjusted under 35 U.S.C. 154(b) by 1177 days.

(21) Appl. No.: 11/694,026

(22) Filed: Mar. 30, 2007

(65) Prior Publication Data

US 2007/0260265 A1  Nov. 8, 2007

(30) Foreign Application Priority Data

Mar. 30, 2006 (DE) .......... 10 2006 016 002

(51) Int. Cl.
 *A61B 17/42* (2006.01)
(52) U.S. Cl.
 USPC ..................................................... 606/119
(58) Field of Classification Search
 USPC .......... 600/204, 201, 210, 217, 219; 604/279;
 606/108, 119–120, 167, 170, 180,
 606/205–208
 See application file for complete search history.

(56) References Cited

U.S. PATENT DOCUMENTS

| 3,995,619 A |   | 12/1976 | Glatzer |
|---|---|---|---|
| 4,461,282 A | * | 7/1984 | Ouchi et al. .................. 600/148 |
| 5,571,115 A |   | 11/1996 | Nicholas |
| 5,709,697 A |   | 1/1998 | Ratcliff et al. |
| 5,746,750 A |   | 5/1998 | Prestel et al. |
| 5,980,534 A |   | 11/1999 | Gimpelson |
| 6,110,127 A | * | 8/2000 | Suzuki .......................... 600/565 |

FOREIGN PATENT DOCUMENTS

| DE | 196 03 981 | 8/1997 |
|---|---|---|
| DE | 201 10 921 | 12/2001 |
| GB | 467229 | 6/1937 |
| WO | WO 02/065924 | 8/2002 |

OTHER PUBLICATIONS

Catalogue "Storz, Die Welt Der Endoskopie, Laparoskopie", 5$^{th}$ Edition Jan. 2005, p. 328 (device No. 26168 QN) and p. 339 (device No. 26168 D).
European Search Report, Jul. 16, 2007, 5 pages.

* cited by examiner

*Primary Examiner* — Ashley Fishback
(74) *Attorney, Agent, or Firm* — St. Onge Steward Johnston & Reens LLC

(57) ABSTRACT

A device serves for performing examination and surgical intervention on the uterus. The device comprises an approximate rod-shaped body and an extension piece protruding from a distal end of said body. Said extension piece can be introduced in a cervical canal of an uterus. At least one adjustable jaw part for fixing of a cervical tissue between said extension piece and said jaw part is provided. An operating device serves for operating said adjustable jaw part. Said operating device is arranged on said rod-shaped body in such a way that a hand of an operator gripping said body can operate said operating device.

14 Claims, 8 Drawing Sheets

DEVICE FOR PERFORMING EXAMINATIONS AND SURGICAL INTERVENTIONS ON THE UTERUS

BACKGROUND OF THE INVENTION

The invention relates to a device for performing examinations and surgical interventions on the uterus.

A device of this kind in the form of uterine forceps is known from the catalogue published by Karl Storz GmbH & Co. KG, Tuttlingen, "STORZ, DIE WELT DER ENDOSKOPIE, LAPAROSKOPIE", 5th edition January 2005, page 328 (device number 26168 QN).

Such devices are used in the medical field for examining and for performing surgical interventions on the uterus.

For this purpose, the extension piece arranged at a distal end of the device is introduced through the vagina into the cervical canal. The extension piece lying in the cervical canal is used to mobilize the uterus. If an irrigation channel is additionally provided, the uterus can be irrigated. Examinations and other manipulations are performed using another device, for example in a hysterectomy.

A uterine manipulator, Clermont-Ferrand model, is known from the catalogue published by Karl Storz GmbH & Co. KG, Tuttlingen, "STORZ, DIE WELT DER ENDOSKOPIL, LAPAROSKOPIE", 5th edition January 2005, page 339 (device number 26168 D). This uterine manipulator is composed of an approximately rod-shaped body. The proximal end has a pivotable grip with a gripping bracket to be enclosed by the hand. A pivotable extension piece is arranged at the distal end. The extension piece and the gripping bracket are connected to one another such that a pivoting of the gripping bracket causes a pivoting of the extension piece. With a second hand, the uterine manipulator is gripped either at its body or at a rod protruding laterally from the latter, in order in this way to hold the approximately 50 cm long manipulator.

The desired angle of the extension piece relative to the elongate body is adjusted via the gripping bracket and can be locked by a locking mechanism in five locked positions between 0° and 90°. In addition to mobilizing the uterus, it is also possible to identify the vault by means of the manipulator rod being advanced in the proximal direction. The uterine manipulator is also equipped with a sealing system, which ensures that $CO_2$ introduced into the uterus after opening of the vaginal vault cannot escape.

This uterine manipulator is very wide, very long and requires both hands for use.

The use of this uterine manipulator is limited to manipulation of the uterus and identification of the vault. For visual examinations or surgical interventions, further devices in addition to the uterine manipulator have to be guided through the vagina to the uterus. This is very uncomfortable for the patient and is also difficult for the physician to do, since he has to operate two devices simultaneously.

It is object of the present invention is therefore to make available an easy-to-use device for performing examinations and surgical interventions of this kind on the uterus.

SUMMARY OF THE INVENTION

According to the invention, this object is achieved by a device having an approximately rod-shaped body, an extension piece protruding from a distal end of said body, said extension piece can be introduced in a cervical canal of an uterus. At least one adjustable jaw part serves for fixing of a cervical tissue between the extension piece and the jaw part. An operating device is provided for operating said adjustable jaw part. The operating device is arranged on that rod-shaped body in such a way, that a hand of an operator gripping said body can operate said operating device.

These measures have the considerable advantage, among others, that the rod-shaped body of the device corresponds to the anatomical shape of the vagina, and the device is easy to introduce through the vagina into the cervical canal.

The rod-shaped body can be gripped by a human hand. The palm of the hand and the fingers close firmly around the rod-shaped body. In this way, not only can the body be gripped very firmly and securely, it can also be done in a way that takes up little space. With a rod-shaped body gripped by one hand, the field of view is obstructed to a much lesser extent than it is when gripping a scissor-type forceps with finger eyelets.

Since the gripping hand grips the rod-shaped body, the hold of the device is much more stable and firm. The operating device for moving the jaw part is arranged on the body in such a way that it can be actuated by the hand, for example by a finger, that has gripped the body. In doing so, the body still remains gripped by the hand and can thus be held firmly and securely. This permits handling of the device using just one hand.

The rod-shaped body, gripped by one hand, can be gently introduced into the vagina by the operator. In doing so, the jaw part is initially placed tight against the extension piece via the operating device. The extension piece extends distally away from the rod-shaped body and forms a rigid unit with the latter. Consequently, it can be introduced safely through the vagina and advanced as far as the cervix.

Before the extension piece is introduced into the cervix, the jaw part can be moved laterally slightly away from the extension piece.

After the extension piece has been inserted into the cervix, the jaw part is moved for positional fixing, as a result of which cervical tissue is clamped between extension piece and jaw part.

All these procedures can be performed using just one hand, namely the hand that has gripped the body. By virtue of the ergonomic arrangement of the operating device, the jaw part can be easily controlled using the same hand and in a way that takes up little space.

In another embodiment of the invention, a channel is provided that extends right through the body.

This measure has the advantage that a further additional medical instrument, for example an endoscope, can be guided into and through the channel extending through the body.

By virtue of the fact that two devices do not have to be introduced alongside one another through the vagina and into the cervix, and that the second device or further devices can instead be pushed through the device channel, this procedure is much more comfortable for the patient, and is also easier for the operator, since the latter no longer has to introduce a second device alongside a device already located in the vagina, but can instead guide this further device through the already inserted device. This channel can also be used for other purposes, for example simply for irrigation or the like.

In another embodiment of the invention, the proximal end of the body has a handgrip, and the operating device is arranged between the rod-shaped body and the handgrip.

This measure has the advantage of creating a particularly slender structure adapted to the anatomy of the vagina. The device therefore being able to be introduced in a way that does not cause the patient discomfort. At the same time, the handling is also made very ergonomic for the operator, since the device can be introduced with the distal rod into the vagina, while the operating device and the handgrip remain outside the body.

In another embodiment, the operating device can be actuated by a hand that has gripped the body, by means of moving an element.

The element can be moved by turning, sliding or pressing it.

This measure has the advantage that the control of the movement of the jaw part is obtained by particularly ergonomic means, namely by moving an element. As before, the device can be held securely by the hand gripping it, such that moving the jaw part also requires only one hand.

In another embodiment of the invention, the element of the operating device can be actuated by a thumb of the gripping hand.

This measure has the advantage that only the thumb has to be used to control the movement of the jaw part, while the palm of the hand and the remaining fingers are available, as before, for holding the device.

In another embodiment of the invention, the element is designed as a ring element.

This measure has the advantage that such an element can, without visual contact or great concentration, be gripped by a finger, for example by the thumb, and correspondingly moved for the manipulations.

In another embodiment of the invention, a depression for placement of the thumb is formed in the ring element.

This measure has the considerable advantage that the depression can be easily sensed by the thumb without visual contact, and, after the thumb is placed in the depression, it is guaranteed a secure fit for actuating the operating device.

In another embodiment of the invention, the operating device is operatively connected to the jaw part in such a way that turning of the operating device causes a pivoting of the jaw part.

This measure has the considerable advantage that no spreading-out movements, for example as in the case of scissors, are performed in order to move the jaw part. Only a rotation movement around the body has to be effected. Turning the operating device about a rod-shaped body is mechanically very simple and can be done reliably, such that the handling is considerably simplified. Nor does the system have any inherent risk of tilting or the like, since the device, as before, lies gripped in the operator's hand. The operating device simply has to be turned, for example only with the thumb, and this can be made even easier by the latter being placed in a depression formed on a rotation ring.

In another embodiment of the invention, the operating device is operatively connected to a helical groove of a sliding sleeve, such that turning of the operating device causes an axial displacement of the sliding sleeve along the body.

This measure has the advantage that a rotation movement of the operating device can be very easily converted mechanically into an axial displacement of the sliding sleeve, which itself can be safely guided along the rod-shaped body. The sliding sleeve is then correspondingly connected to the jaw part.

By this measure, the rotation movement of the operating device can be converted into an axial sliding movement in a way that takes up little space.

In another embodiment of the invention, the sliding sleeve is connected to an actuating element in such a way that a linear movement of the sliding sleeve can be converted into a pivoting movement of the jaw part towards or away from the extension piece.

This measure has the considerable advantage that, by measures that take up little space, the linear movement of the sleeve can be converted into a pivoting movement of the jaw part. The actuating element can be guided along the rod-shape body to the jaw part.

In another embodiment of the invention, the actuating element is connected at the distal end to a ring which is pivotable about an axis extending transverse to the longitudinal axis of the body, the ring supporting the distally protruding jaw part.

This measure has the advantage that, in order also to pivot the jaw part, a structural element, namely a ring, is used which adapts favourably to the overall form of the rod-shaped body. Thus, it does not require any structural elements protruding from the body or emerging during a movement of the jaw part. Both the sliding sleeve and also the axially extending actuating element and the pivotable ring can be integrated into the geometry of the rod-shaped body.

In another embodiment of the invention, there are two adjustable jaw parts lying opposite one another.

This has the advantage that, by means of the jaw parts lying opposite one another at two points, tissue of the cervix can be clamped between jaw part and extension piece, such that the device is held firmly and securely. This also opens up the possibility of releasing the device from the hand, and then carrying out other manipulations with both hands, or for example inserting other instruments through the device.

In another embodiment of the invention, two rings are provided which are pivotable about a common axis, each of them supporting a jaw part, and each ring is connected to the sliding sleeve via an actuating element.

This measure has the advantage that the two jaw parts can be pivoted synchronously, and that both law parts can be pivoted simultaneously through the linear displacement of the sliding sleeve via the actuating elements. The rings are arranged concentrically and are pivotable about a common axis. This measure has the advantage that a compact structure that takes up little space can be achieved at the distal end area of the device.

In another embodiment of the invention, the operating device is provided with a locking mechanism via which the operating device, and thus a jaw part, can be locked in a defined position relative to the extension piece.

This measure has the advantage that the jaw parts can be locked in defined pivot positions, such that, for example when tissue is clamped sufficiently securely between jaw part and extension piece, this position is retained via the locking mechanism. In this way, the operator can then release the device, as previously mentioned, in order to perform other manipulations.

In another embodiment of the invention, the locking mechanism has a catch arranged in the operating device.

This measure has the advantage that the catch, like the operating device, can be actuated ergonomically, for example by the thumb of one hand that has gripped the device.

In another embodiment of the invention, the extension piece is designed as a cone through which the channel extends.

This measure has the advantage that, by way of the distal outlet opening of the cone, and thus of the channel, other instruments can be guided in a specifically targeted manner through the device. The cone facilitates insertion into the cervical canal.

In another embodiment of the invention, a jaw part has at least one tip directed towards the extension piece.

This measure has the advantage that the tissue between law part and extension piece can be held particularly firmly by the tips.

In another embodiment of the invention, the jaw parts are pivotable relative to the positionally fixed extension piece.

This measure has the advantage that, during actuation of the jaw parts, the extension piece remains in place, for example having already been inserted into the cervical canal, and only the jaw parts move relative to it. This too contributes to simple and secure handling.

In another embodiment of the invention, markings are provided on the body and on the operating device movable relative to the latter, and the relative position of the markings provides an indication of the respective pivoting position of the at least one jaw part with respect to the extension piece.

This measure has the considerable advantage that the operator is provided with an indication of how far or how close a jaw part is to the extension piece.

As long as no viewing instrument has been introduced, the distal end area is located at the end of the vagina, at the transition to the uterus, an area that can be viewed only with difficulty. The markings now give the operator a sense of how far the jaw parts, that he can see only with difficulty, have been moved, such that the device can be fixed on the cervical tissue non-traumatically, without the risk of the jaw parts being driven too deep into the tissue and damaging the latter.

It will be appreciated that the aforementioned features and those still to be explained below can be used not only in the cited combinations, but also in other combinations, without departing from the scope of the present invention.

BRIEF DESCRIPTION OF THE DRAWINGS

The invention is described and explained below in more detail on the basis of a selected illustrative embodiment and with reference to the drawings, in which.

DETAILED DESCRIPTION OF PREFERRED EMBODIMENTS

A device shown in the figures and used for performing examinations and surgical procedures on the uterus is designated in its entirety by reference number 10.

Figure 1:
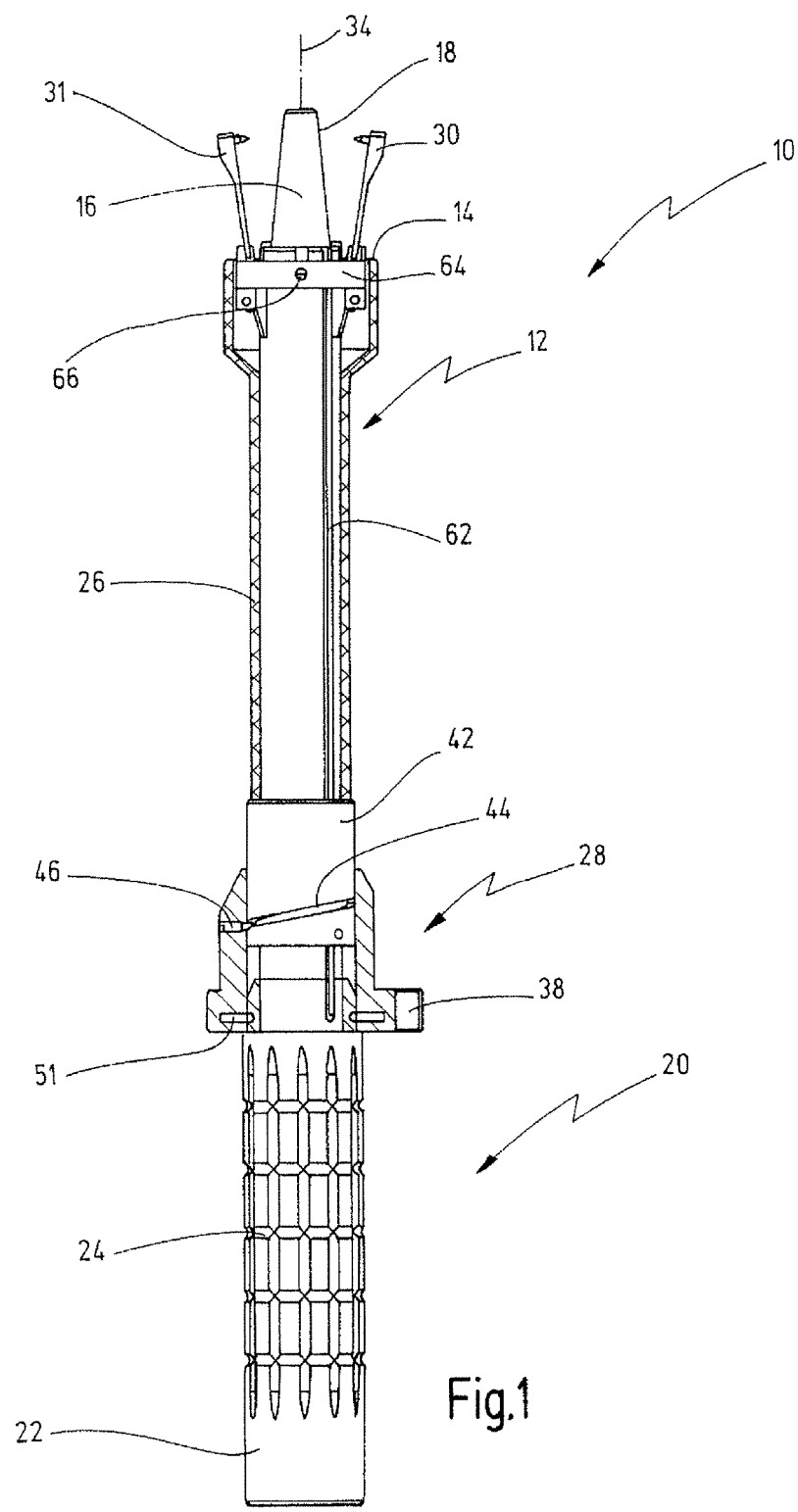
FIG. 1 shows a partially cutaway side view of a device according to the invention.
Figure 2:
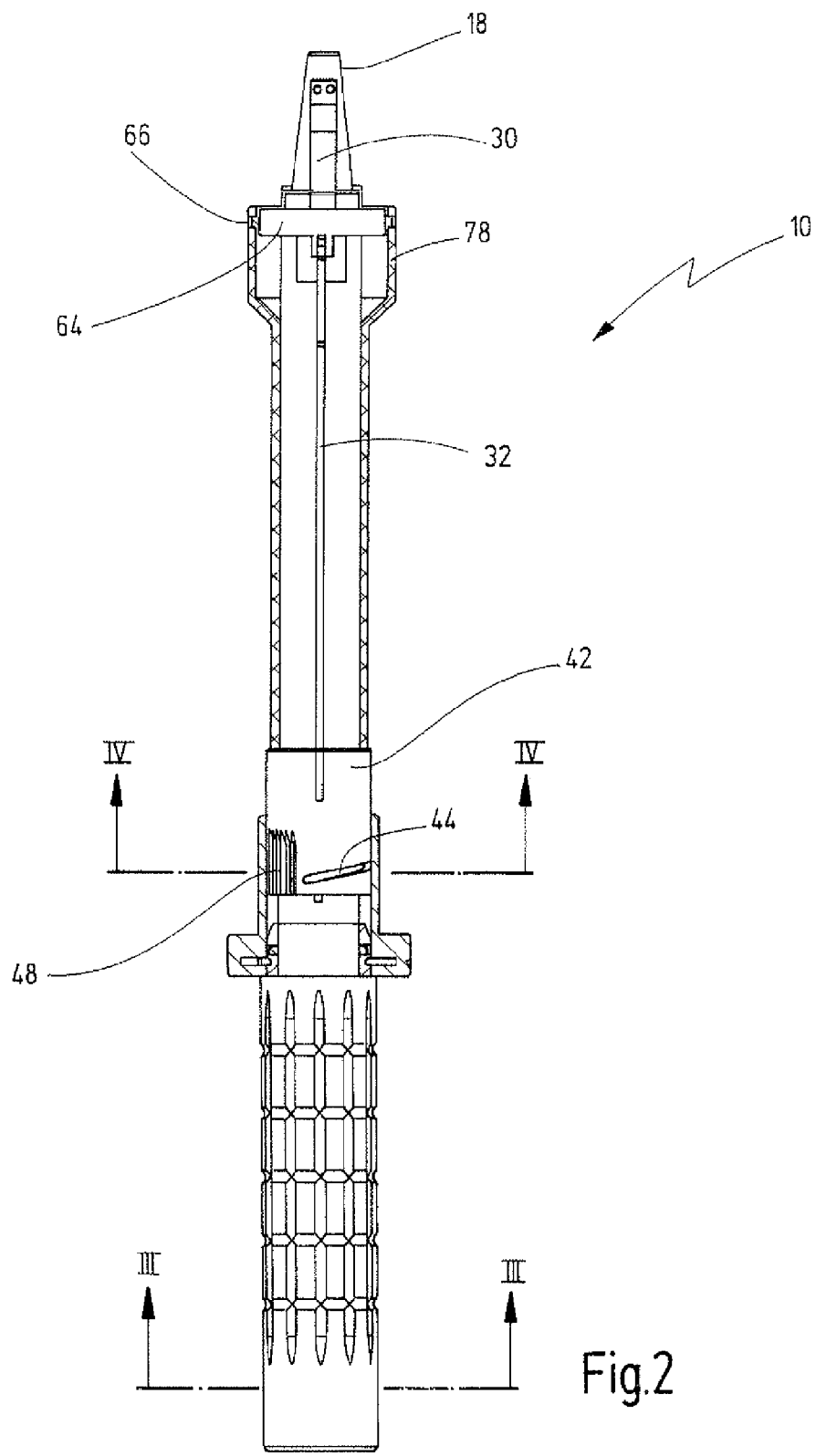
FIG. 2 shows a view corresponding to the view in FIG. 1, but turned through 90 degrees about the longitudinal axis of the device.

As is shown particularly in FIGS. 1 and 2, the device 10 has a rod-shaped body 12, from whose distal end 14 an extension piece 16 protrudes.

In the illustrative embodiment shown, the extension piece 16 is designed as a cone 18.

A proximal end area 20, covering just over a third of the total length of the device 10, is designed as a handgrip 22. A notched pattern 24 is cut into the outer surface, such that the device 10 can be gripped firmly and securely by a human hand in the area of the handgrip 22. The remaining part of the body 12 is designed as a rod 26, the outer surface of which is smooth. At the distal end, the rod 26 has a widened portion 78 in which, as will be explained in more detail below, further structural parts are received.

An operating device 28 is arranged between rod 26 and handgrip 22.

The operating device 28 is used to move two jaw parts 30 and 31 arranged opposite one another at the distal end 14 of the rod 26.

FIG. 1 shows a position in which the jaw parts 30, 31 are spread or pivoted to the maximum extent away from the extension piece 16. By actuation of the operating device 28, the two jaw parts 30 and 31 can be moved or pivoted towards the extension piece 16 until they almost touch the latter.

Figure 3:
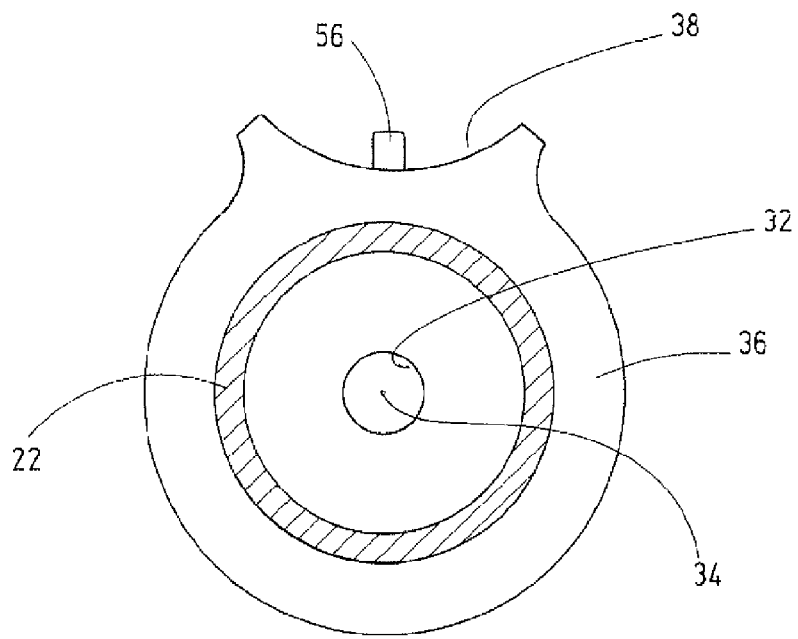
FIG. 3 shows a cross section along line III-III in FIG. 2.

Extending centrally through the device 10 there is a channel 32 whose central longitudinal axis corresponds to the longitudinal axis 34 of the device 10 (FIG. 3).

The design of the operating device 28 will first be described in more detail with reference to FIGS. 1 to 5.

The operating device 28 has a ring element 36 whose external diameter is slightly greater than the external diameter of the handgrip 22 (FIG. 3).

A depression 38 is formed in the ring element 36, and a thumb of a human hand that has gripped the handgrip 22 can be placed in the depression 38 of the ring element 36.

Extending from the distal end of the ring element 36 there is a sleeve 40, which surrounds a sliding sleeve 42 partially received therein.

On its outer face, the sliding sleeve 42 has a helical groove 44 in which runs a pin 46 protruding radially inwards from the sleeve 40 of the ring element 36.

The sliding sleeve 42 is mounted in a longitudinally displaceable manner on the outer face of the rod 26. Bolts 51 protrude from the inner face of the operating device 28 and engage in a circumferential annular groove (not shown here) of the body 12.

Consequently, a rotation movement of the ring element 36 can be converted via the pin 46 and the helical groove 44 into an axial displacement of the sliding sleeve 42 along the longitudinal axis 34 of the device 10.

Figure 4:
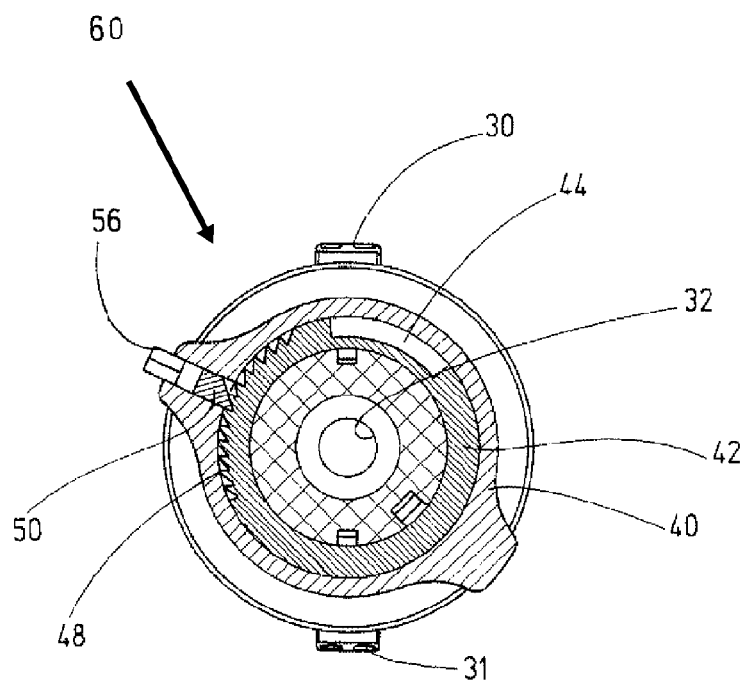
FIG. 4 shows a cross section along line IV-IV in FIG. 2.

As can be seen in particular from FIG. 2 and from the cross-sectional view in FIG. 4, index notches 48 are cut on the outer face of the sliding sleeve 42, and a catch 50 comes into engagement in these notches 48.

Figure 5:
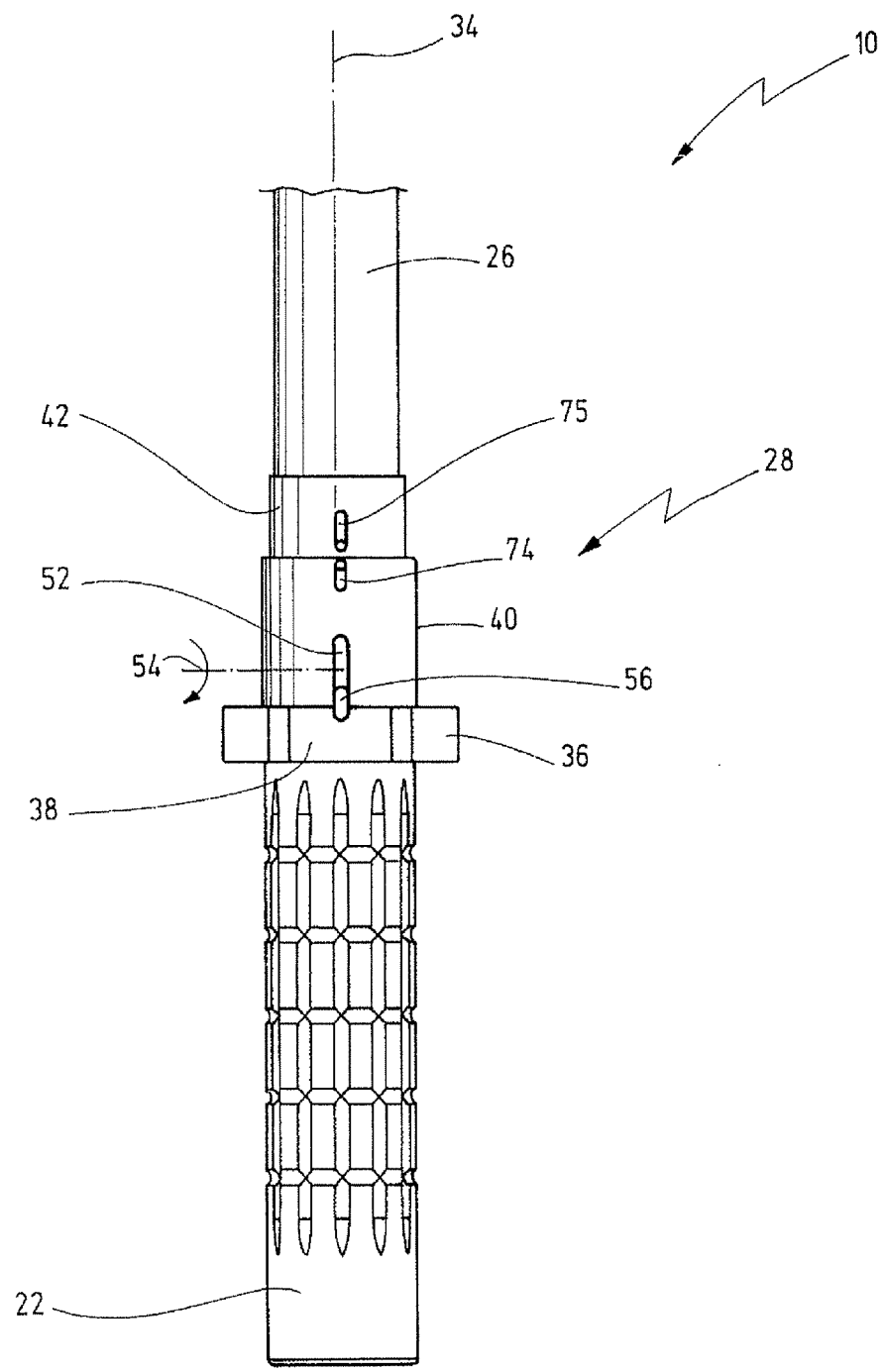
FIG. 5 shows a side view of part of the device in the area of the handgrip and of the operating device.

The catch 50 is designed as a two-armed lever 52, as can be seen in particular from FIG. 5, which can be pivoted or tilted about an axis 54 transverse to the longitudinal axis 34 of the device 10.

One arm of the lever 52 supports the catch 50, which is in engagement with the index notches 48, and the opposite arm of the lever 52 has a radially outwardly protruding pusher 56.

It will be seen from the plan view in FIG. 5 that the pusher 56 extends into the depression 38.

Thus, the index notches 48 interact with the catch 50, and with the latter's actuating element 52, as a locking mechanism 60.

This locking mechanism 60 can be actuated by the same finger, for example the thumb, which also turns the ring element 36. To do so, pressure is applied to the pusher 56, such that the lever 52 is then pivoted counter to the force of a spring (not shown here), such that the catch 50 disengages from the index notches 48.

As can be seen in particular from the cross-sectional views in FIGS. 1 and 2, the sliding sleeve 42 is connected to rod-shaped actuating elements 62, 63 that extend distally in the axial direction.

At the distal end, the actuating elements 62, 63 are connected to respective rings 64, 65 whose planes lie in a cross-sectional plane transverse to the longitudinal axis 34 of the body 12.

The rings 64 and 65 are arranged coaxially one within the other and are pivotable about a common axis 66.

Figure 6:
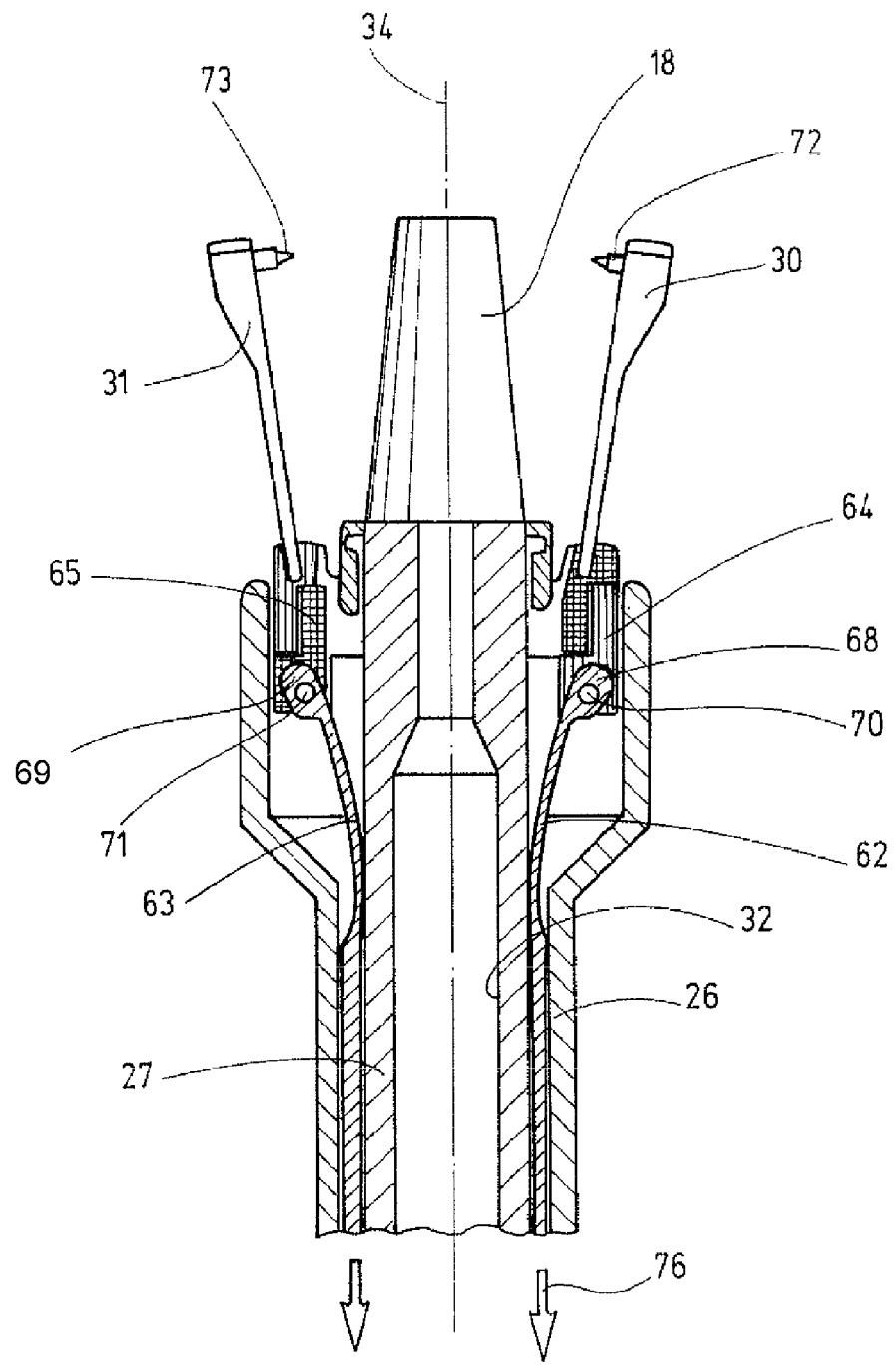
FIG. 6 shows an enlarged longitudinal section in the area of the distal end area of the device, with the jaw parts pivoted away from the extension piece.
Figure 7:
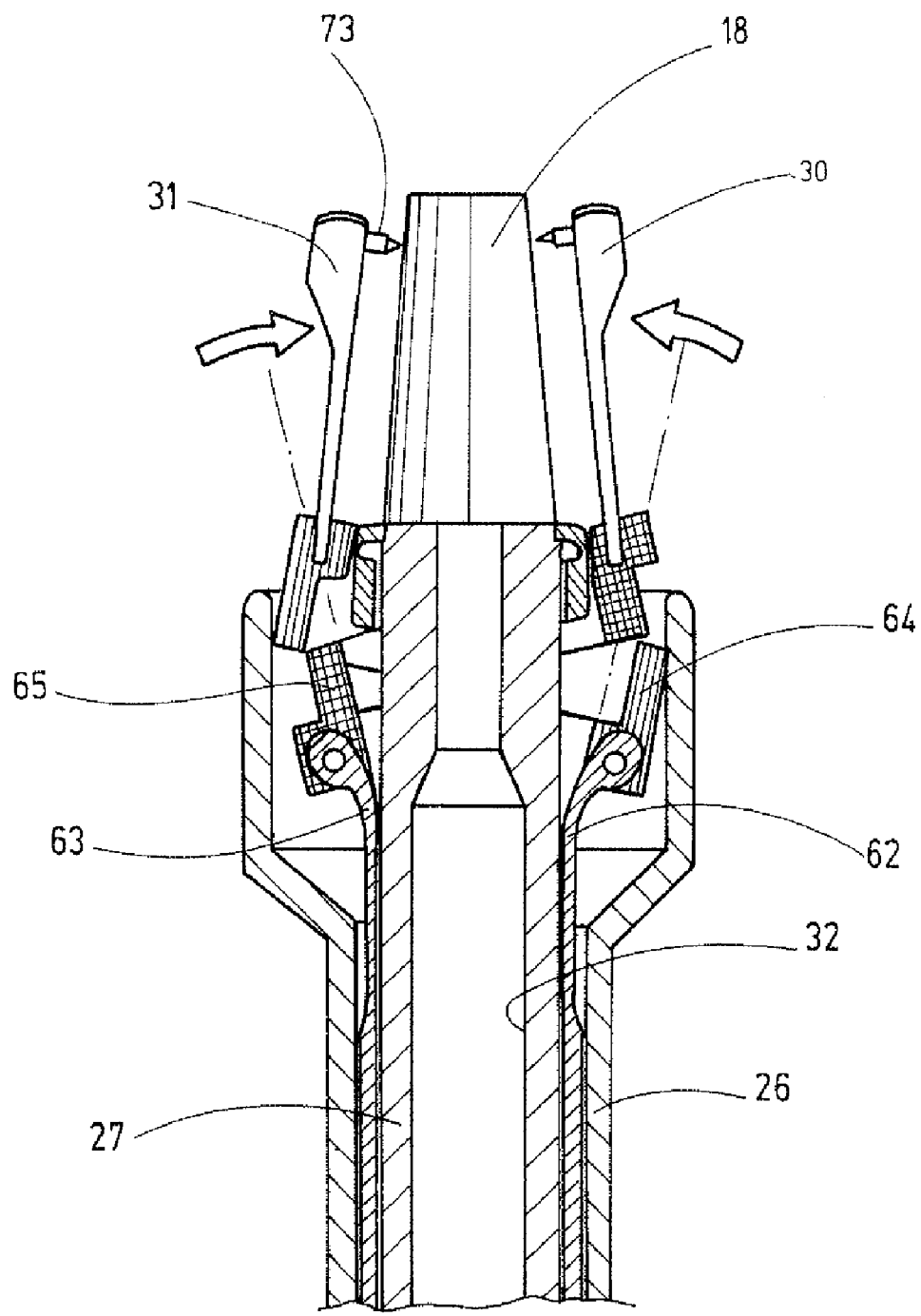
FIG. 7 shows the view of FIG. 6, with the jaw parts pivoted onto the extension piece.

From the enlarged views in FIGS. 6 and 7, it will be seen that each actuating element 62, 63 is connected distally to one of the rings 64 and 65 via respective brackets 68, 69 and eyelets 70, 71. Each ring 64, 65 supports a distally protruding jaw part 30, 31, respectively. The jaw parts 30, 31 are arranged diametrically opposite one another at the location where the actuating element 62, 63 is connected to the respective ring 64, 65.

FIG. 6 shows a situation in which the two rings 64 and 65, lying one within the other, are oriented in one plane. This is the spread-open position of the jaw parts 30 and 31.

If the sliding sleeve 42 is now displaced in the proximal direction, by turning the ring element 36 of the operating device 28, the two actuating elements 62 and 63 are also displaced in the proximal direction, as is indicated by the arrows 76 in FIG. 6.

In this way, the two rings 64 and 65 are tilted, specifically about their common axis 66 (see FIG. 1), as a result of which the jaw parts 30 and 31 are then pivoted towards the extension piece 16.

This situation is shown in FIG. 7, i.e. the two jaw parts 30 and 31 have been pivoted until their radially inwardly protruding tips 72, 73 have reached the outer face of the extension piece 16.

By means of the locking mechanism described above, the jaw parts 30 and 31 can now be locked in numerous intermediate positions between the end positions in FIGS. 6 and 7.

The inclination of the index notches 48 is oriented such that the bevelled catch 50 can run over the index notches 48 when the law parts 30 and 31 are moved from the position in FIG. 6 to the position in FIG. 7. That is to say, the catch 50 impedes the reverse movement, i.e. the movement from FIG. 7 to FIG. 6. To permit this movement, the pusher 56 has to be pressed and the catch 50 has to disengage from the corresponding index notch 48.

It will be seen from the plan view in FIG. 5 that bar-shaped markings 74, 75 are present on the outer face of the sleeve 40 of the operating device 28 and on the outer face of the sliding sleeve 42. The relative position of the markings 74 and 75 with respect to each other shows the operator a defined pivot position of the jaw parts 30, 31 relative to the extension piece 16.

Thus, for example, the relative position of the markings 74 and 75 shown in FIG. 5, that is to say in linear orientation, can represent the maximum outwardly pivoted position of the jaw parts 30 and 31, as is shown in FIG. 6.

When the operating device 28 is actuated, the sleeve 40 is turned about the longitudinal axis 34, whereas the sliding sleeve 42 is not turned. This means that, for example, the marking 74, if turned clockwise, moves to the right relative to the marking 75. The distance between the markings shows the operator how far the jaw parts 30, 31 are pivoted inwards.

It is also possible for this to be configured exactly the opposite way round, i.e. when the markings 74 and 75 are in alignment, the jaw parts 30, 31 are closed to the maximum extent.

It will be seen from the cross-sectional views in FIG. 6 and FIG. 7 that the controls for the rings 64, 65 are received in a widened portion 78 at the distal end of the rod 26.

With the jaw parts 30, 31 applied against the extension piece 16, as shown in FIG. 7 for example, the device 10 is introduced into a human vagina. The rod-shape design of the body 12 makes this very easy and means it can be done in a manner that does not cause the patient discomfort. The operator holds the device 10 by gripping the handgrip 22 in the hand.

Figure 8:
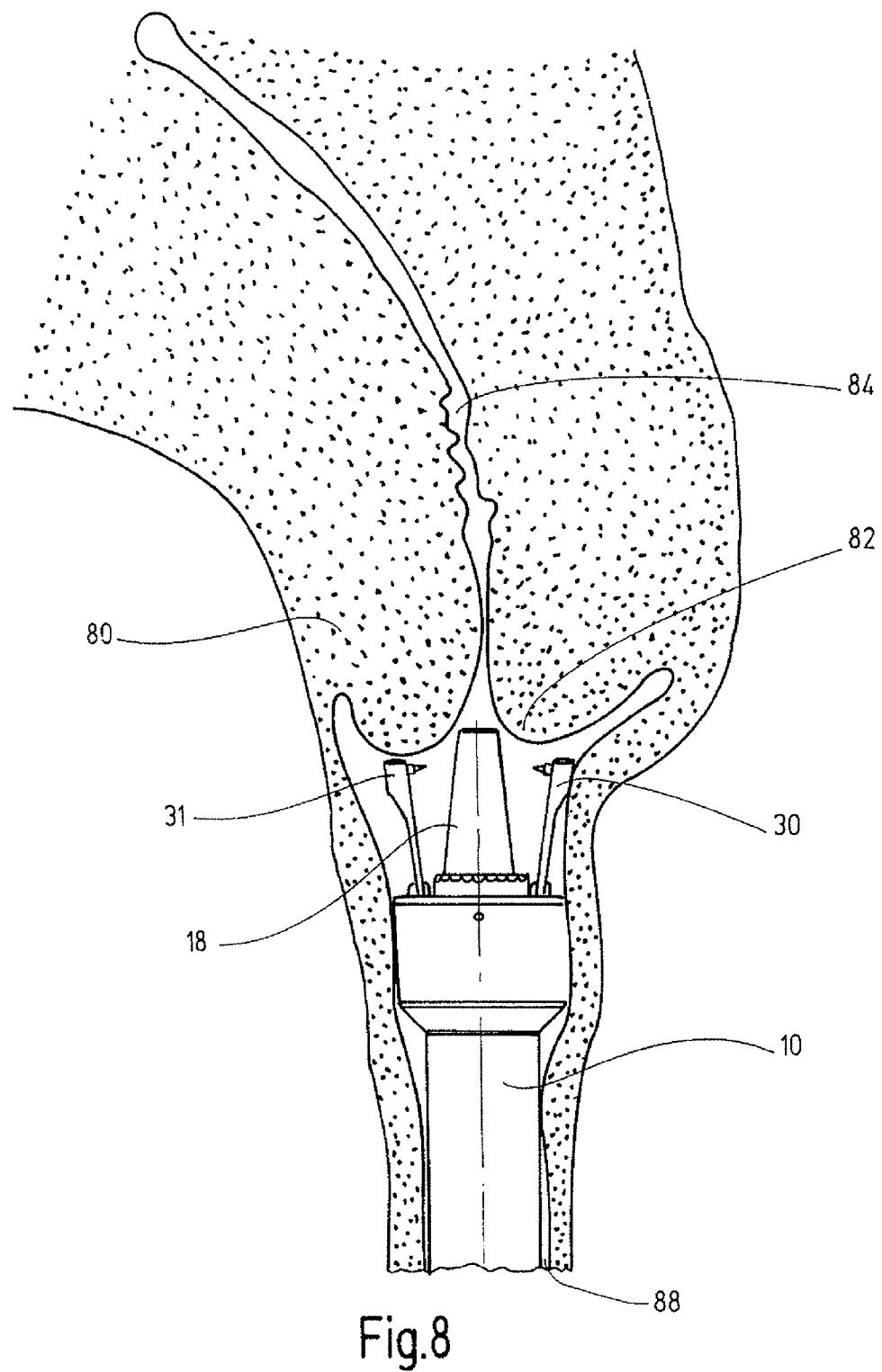
FIG. 8 shows a cross section through the lower abdomen of a patient in the area of the vagina and of the uterus, the device according to the invention having been guided as far as the cervix.

FIG. 8 shows a situation in which the device 10 is pushed through the vagina 88 as far as the cervix 82 of a uterus 80.

Figure 9:
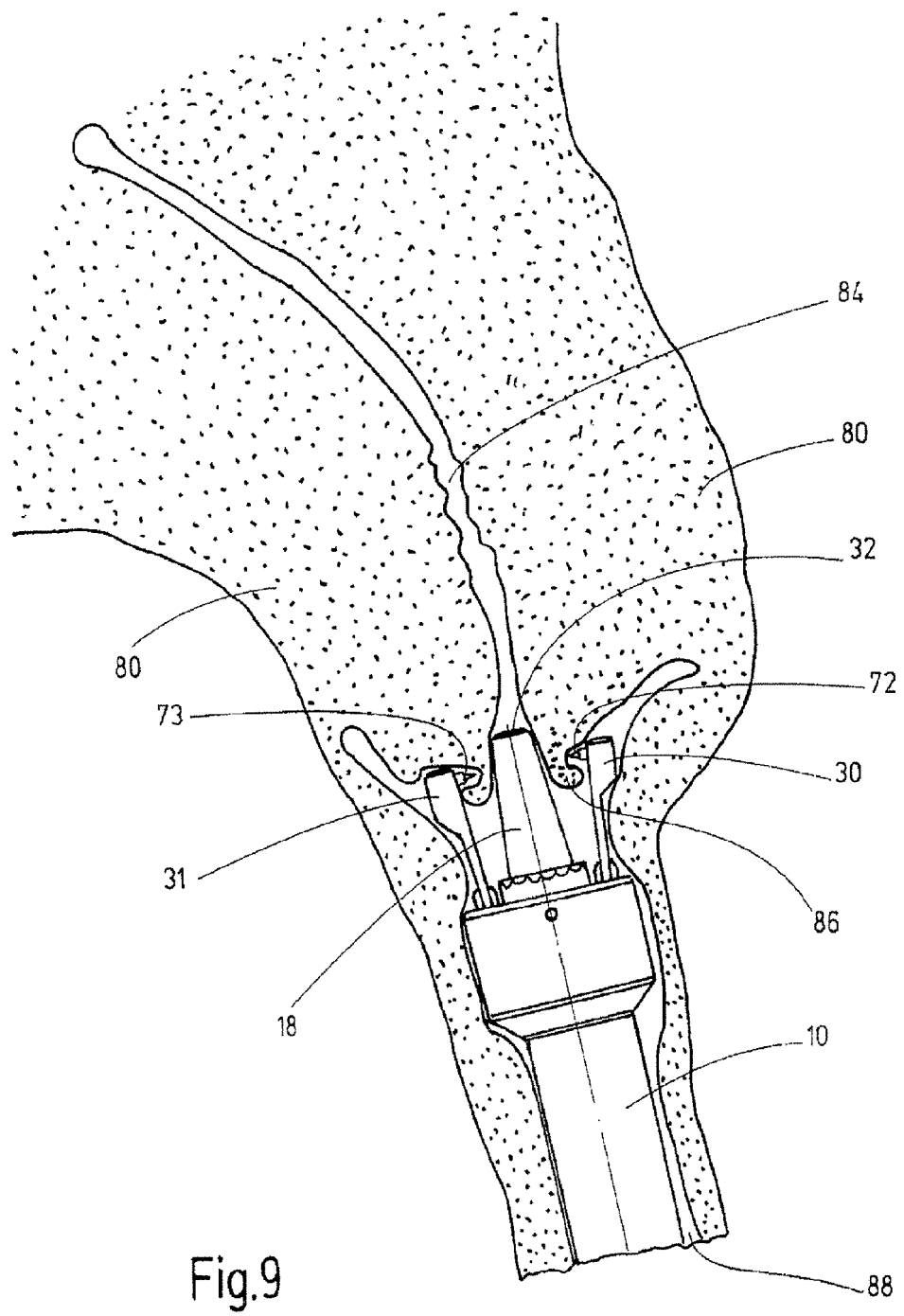
FIG. 9 shows a cross-sectional view which corresponds to the cross-sectional view in FIG. 8 and in which the extension piece of the device has been pushed into the cervix, the jaw parts have been pivoted onto the extension piece, and tissue is clamped between these.

By turning the operating device 28, the jaw parts 30, 31 are spread apart from the cone 18, such that the latter can be advanced further into the cervical canal 84. Tissue 86 then comes between the spread-out jaw parts 30 and 31 and the cone 18. By renewed actuation of the operating device 28, the jaw parts 30 and 31 can now be moved towards the cone 18 until, as is shown in FIG. 9, tissue 86 is fixed in the area of the cervix 82, between the latter and the extension piece 16. By means of the aforementioned locking mechanism 60, the jaw parts 30 and 31 remain in this relative position.

This means the device 10 is now fixed in position on the cervix 82.

Further procedures can now be performed through the central channel 32.

For example, an irrigation fluid can be guided through it. An endoscope, for example, can be guided through in order to carry out visual examination in the cervical canal 84.

Instruments can also be introduced, for example in order to remove cysts or ulcers or the like from the cervical canal 84.

These procedures can all be performed centrally through the channel 32 of the device 10, with the latter being held firmly and securely on the cervix 82 by the jaw parts 30 and 31.

What is claimed is:

1. A device for performing examinations and surgical interventions on a uterus, comprising:
   an approximately rod-shaped body having a proximal end and a distal end,
   an extension piece attached to the distal end of said rod-shaped body, said extension piece configured to be introduced in a cervical canal of a uterus,
   two adjustable jaw parts lying opposite one another for fixing of a cervical tissue between said extension piece and said two jaw parts, and
   an operating device for operating said two adjustable jaw parts,
   said operating device is operatively connected to said two jaw parts by a sliding sleeve, a turning of said operating device causes an axial displacement of said sliding sleeve along said rod-shaped body,
   said sliding sleeve being connected to two actuating elements each of which being connected at a distal end to a respective ring, each of said respective rings being pivotable about an axis extending transverse to a longitudinal axis of said rod-shaped body, each ring supporting one jaw part protruding distally from said ring, said rings being pivotable about a common axis,
   an axial displacement of said sliding sleeve causes a rotation of each ring about said common axis and thereby a lateral movement of said two jaw parts.

2. The device of claim 1, wherein a channel is provided extending right through said rod shaped body.

3. The device of claim 2, wherein said extension piece is designed as a cone and said channel extends through said cone.

4. The device of claim 1, wherein said operating device is configured to be actuated by a hand gripping said rod shaped body by means of moving of an element of an actuating device.

5. The device of claim 4, wherein said element is configured to be actuated by a thumb of said hand gripping said device.

6. The device of claim 5, wherein said element is designed as a ring element.

7. The device of claim 6, wherein a depression for placement of a thumb is formed in said ring element.

8. The device of claim 1, wherein said operating device is provided with a locking mechanism via which said operating device and thus said two jaw parts can be locked in a defined position relative to said extension piece.

9. The device of claim 8, wherein said locking mechanism has a catch arranged in said operating device.

10. The device of claim 1, wherein each of said two jaw parts has at least one tip directed towards said extension piece.

11. The device of claim 1, wherein said extension piece is positionally fixed and said two pivotable jaw parts are adjustable relative to said extension piece.

12. The device of claim 1, wherein markings are provided on said rod-shaped body and on said operating device which is movable relative to said rod-shaped body, a relative position of said markings provides an indication of a respective position of said two jaw parts with respect to said extension piece.

13. The device of claim 1, wherein a proximal end of said rod shaped body has a handgrip and wherein said operating device is arranged between said handgrip and said rod-shaped body.

14. The device of claim 1, wherein said two adjustable jaw parts are arranged around the extension piece, such that a proximal end of the two adjustable jaw parts are located at the distal end of said rod-shaped body.

* * * * *